United States Patent

Fukumoto et al.

[11] Patent Number: 5,880,318
[45] Date of Patent: Mar. 9, 1999

[54] PROCESS FOR THE PREPARATION OF α-BROMO, ω-CHLOROALKANES

[75] Inventors: Takehiko Fukumoto; Hiroshi Suzuki, both of Niigata-ken; Kinya Ogawa, Tokyo; Kazushi Hirokawa, Niigata-ken, all of Japan

[73] Assignee: Shin-Etsu Chemical Co., Ltd., Tokyo, Japan

[21] Appl. No.: 906,816

[22] Filed: Aug. 6, 1997

[30] Foreign Application Priority Data

Aug. 13, 1996 [JP] Japan ................................. 8-213455

[51] Int. Cl.⁶ ..................................................... C07C 19/00
[52] U.S. Cl. ............................ 570/260; 570/256; 570/261
[58] Field of Search ..................... 570/256, 260, 570/261

[56] References Cited

U.S. PATENT DOCUMENTS 3,799,999  3/1974  Gordon et al. .
3,914,327  10/1975  Johnson et al. .
3,935,289  1/1976  Ostrowick ............................... 570/261

FOREIGN PATENT DOCUMENTS 718 472  9/1965  Canada ................................... 570/261

OTHER PUBLICATIONS

Roger C. Hahn, "Homogeneous Nucleophile Exchange. 1. Simple, High–Yield Synthesis of Some Heterodihalides", J. Org. Chem, vol. 53, No. 6, pp. 1331–1333 (1988). Syracuse Univ., Dept. of Chem. 13244–1200.

*Primary Examiner*—Alan Siegel
*Attorney, Agent, or Firm*—McAulay Nissen Goldberg Kiel & Hand, LLP

[57] ABSTRACT

Described is a process for easily preparing an α-bromo,ω-chloroalkane which is high in purity represented by the formula: $Br(CH_2)_nCl$ in which n stands for an integer of 4 to 12. The process comprises reacting in an organic solvent an α,ω-dichloroalkane with an αω-dibromoalkane. As the organic solvent, an aprotic nitrogen-containing or sulfur-containing organic solvent having a dielectric constant at 20° C. of 20 or larger, for example, N,N-dimethylformamide, N,N-dimethylacetamide or N,N-dimethylimidazolidinone is preferred.

4 Claims, No Drawings

PROCESS FOR THE PREPARATION OF α-BROMO, ω-CHLOROALKANES

BACKGROUND OF THE INVENTION

This invention relates to a process for preparing, with ease at low cost, an α-bromo,ω-chloroalkane which is useful as an organic synthesis raw material, agricultural chemical or intermediate for pharmaceutical.

In organic synthesis, an α-bromo,ω-chloroalkane is a useful compound indispensable for extending a carbon chain. This compound features that even after a substituent is selectively attached only to one of bromo (—Br) side and chloro (—Cl) side by making use of the difference in the reactivity between them, a target compound can be synthesized using a halogen group on the other side. For example, it is possible to selectively react an organic nucleophilic reagent such as Grignard reagent only with the bromo side of an α-bromo,ω-chloroalkane.

What is important here is a purity of an α-bromo,ω-chloroalkane obtained by the reaction. When it contains an α,ω-dichloroalkane as an impurity, it is, in some cases, inert to the above-described nucleophilic reagent. When it contains an α,ω-dibromoalkane, reaction occurs at both the α position and ω-position of the compound, which inevitably forms new impurities. Accordingly, it is very important to find a method to heighten the purity of an α-bromo,(ω-chloroalkane.

As a conventional method, it is the common practice to prepare an α-bromo,ω-chloroalkane, for example, by chlorinating one (ω-position) of the hydroxyl groups of the corresponding α, ω-dihydroxyalkane with hydrochloric acid or the like and then brominating the remaining hydroxyl group at an α-position with phosphorus(III) bromide or the like as shown by the following reaction scheme:

The above conventional technique is however accompanied with the problem that since it needs selective halogenation of the hydroxyl group only at one side, the yield of an α-bromo,ω-chloroalkane inevitably becomes low relative to the raw material α,ω-dihydroxyalkane. Moreover, even if selective halogenation can be accomplished, disproportionation of the resulting halogen occurs easily without close attention upon distillation and purification, which results in the problem of byproduction of an α, ω-dichloroalkane and α, ω-dibromoalkane as impurities. According to the conventional technique, the scale-up therefore cannot be actualized easily and furthermore, it leads to a cost increase.

An object of the present invention is to overcome the above-described drawbacks of the conventional technique and to provide a process for the preparation of a useful α-bromo,ω-chloroalkane easily at low cost.

SUMMARY OF THE INVENTION

The process of the present invention for preparing an α-bromo,ω-chloroalkane represented by the following formula: $Br(CH_2)_nCl$ in which n stands for an integer of 4 to 12 comprises a step of reacting an α,ω-dichloroalkane with an α,ω-dibromoalkane in an organic solvent.

Examples of the organic solvent preferably used in the present invention include aprotic organic solvents having a dielectric constant at 20° C. of 20 or larger. Among such aprotic organic solvents, nitrogen-containing organic solvents and sulfur-containing organic solvents are particularly preferred. Specific examples of the nitrogen-containing organic solvent include N,N-dimethylformamide, N,N-dimethylacetamide and N,N-dimethylimidazolidinone.

According to the process of the present invention, a high-purity α-bromo,ω-chloroalkane can be isolated easily by fractionation subsequent to the reaction between an α,ω-dichloroalkane and an α,ω-dibromoalkane under heating.

The process according to the present invention is also excellent from the economical viewpoint, because the α,ω-dichloroalkane, α,ω-dibromoalkane and the organic solvent removed by fractionation can be reused.

DETAILED DESCRIPTION OF PREFERRED EMBODIMENTS

In the preparation process of the present invention, α,ω-dichloroalkane and α,ω-dibromoalkane are utilized. They are high in purity, easily available and inexpensive. Each of these compounds is generally prepared by replacing two hydroxyl groups of an α,ω-dihydroxyalkane by the same two halogen groups. As such, products which can be prepared easily, are inexpensive and have high purity have been put on the market. Even in the case where the product put on the market is not available by some reasons, such a product can be prepared easily from an α,ω-dihydroxyalkane.

The α,ωdichloroalkane and α,ω-dibromoalkane used in the present invention are represented by the following formulas: $Cl(CH_2)_2Cl$ and $Br(CH_2)_nBr$, respectively, in which n generally stands for 4 to 12.

The organic solvent to be used in the present invention is selected in consideration of its boiling point or polarity. In this invention, when the reaction between an α,ω-dichloroalkane and an α,ω-dibromoalkane is effected in the presence of an organic solvent at the boiling point thereof, reaction proceeds to some extent. The progress of the reaction, however, is largely influenced by the polarity of the organic solvent. In the present invention, organic solvents having a dielectric constant at 20° C. of 20 or higher is preferred. In other words, it is preferred to carry out the reaction in a solvent of high polarity, because the dielectric constant roughly indicates the polarity. Accordingly, the use of n-hexane (dielectric constant: 1.9), dichloromethane (dielectric constant: 8.9), ethyl acetate (dielectric constant: 6.0) or the like retards the progress of the reaction and is therefore not preferred.

As the organic solvent to be used in the present invention, aprotic and nitrogen- or sulfur-containing ones are more preferred.

Examples of the nitrogen-containing organic solvent include N,N-dimethylacetamide (DMAC) (dielectric constant: 37.78 at 25° C.), N,N-dimethylformamide (DMF) (dielectric constant: 36.7 at 25° C.), N,N-dimethylimidazolidinone (DMI) (dielectric constant: 37.6 at 25° C.), acetonitrile (dielectric constant: 37.5 at 20° C.), propionitrile (dielectric constant: 29.7 at 20° C.), N-methylformamide (NMF) (dielectric constant: 182.4 at 20° C.), N,N-diethylformamide (DEF), N-methylacetamide (NMAC) (dielectric constant: 191.3 at 32° C.), N-methylpropionamide (NMPR) (dielectric constant: 172.2 at 25° C.), N,N,N',N'-tetramethyl urea (TMU) (dielectric constant: 23.06 at 20° C.), N-methylpyrrolidone (NMP) (dielectric constant: 32.0 at 25° C.) and N,N'-dimethylpropylene urea (DMPU).

Examples of the sulfur-containing organic solvent include dimethylsulfoxide (DMSO) (dielectric constant: 48.9 at 20° C.) and sulfolane (dielectric constant: 43.3 at 30° C.).

The reaction proceeds favorably in the presence of, among these organic solvents, N,N-dimethylformamide (which will hereinafter be abbreviated as "DMF"), N,N-dimethyl-acetamide (which will hereinafter be abbreviated as "DMAC") or N,N-dimethylimidazolidinone (which will hereinafter be abbreviated as "DMI"). The above-exemplified organic solvents each has a boiling point of 100° C. or higher, is a chemically stable compound, does not need a cumbersome recovery step and permits a favorable reaction progress under mild conditions.

Here, DMF, DMAC and DMI are represented by the following formulas, respectively.

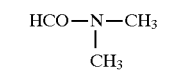 DMF

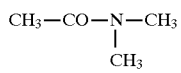 DMAC

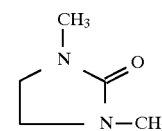 DMI

In the process of the present invention, when an α,ω-dichloroalkane and α,ω-dibromoalkane are mixed and reacted under heat in an organic solvent, exchange of halogens occur, leading to the formation of an α-bromo,ω-chloroalkane with the passage of time. The reaction is reversible and the conversion degree is about 50%. The α,ω-dichloroalkane and α,ω-dibromoalkane are mixed at an equimolar ratio. Even if the ratio is changed, the conversion degree is 50% at the maximum.

In the present invention, the organic solvent is used in an amount of 30 to 300 g, preferably 50 to 200 g relative to the raw materials composed of 1 mole of an α,ω-dichloroalkane and 1 mole of an α,ω-dibromoalkane. The larger the amount of the solvent, the higher the conversion rate, but the final conversion degree remains unchanged. The conversion rate varies depending on the reaction temperature. With a rise in the reaction temperature, the conversion rate becomes higher but at the same time, the decomposition of DMF or DMAC is apt to occur so that the reaction temperature is desired to be 60 to 200° C., particularly 60 to 150° C. The conversion rate by a solvent is large in the order of DMF, DMAC and DMI.

After the reaction, the reaction mixture except for the solvent comprises 50% of an α-bromo,ω-chloroalkane, 25% of an α,ω-dichloroalkane and 25% of an α,ω-dibromoalkane. The α-bromo,ω-chloroalkane can be isolated by separating the reaction mixture by distillation of the reaction mixture in the order of the boiling point. Described specifically, first the solvent is recovered at a low boiling point, and then α,ω-dichloroalkane, α-bromo,ω-chloroalkane and α,ω-dibromoalkane are recovered in this order. This reaction system contains a very small amount of impurities and is therefore stable so that if there is a rectifying column with a proper number of plates, distillation can be carried out easily and moreover, scale-up can be effected. The solvent, α,ω-dichloroalkane and α,ω-dibromoalkane can be reused after being recovered, which makes this process very economical.

EXAMPLE 1

Synthesis of 1-bromo-5-chloropentane

In a reactor, 141 g (1 mole) of 1,5-dichloropentane, 230 g (1 mole) of 1,5-dibromopentane and 100 g of DMF were charged, followed by stirring at 100° C. for three hours under a nitrogen gas atmosphere. After the completion of the reaction, the reaction mixture was analyzed by gas chromatography. As a result, the reaction mixture was found to comprise 20.5% of DMF, 19.1% of 1,5-dichloropentane, 41.4% of 1-bromo-5-chloropentane and 19.0% of 1,5-dibromopentane. The conversion degree was 52.0%.

The reaction mixture was then fractionated by a rectifying column, whereby 1-bromo-5-chloropentane was isolated as shown in Table 1. In Table 1, the boiling points of Fraction 1, Fraction 2, Fraction 3, Fraction 4 and Fraction 5 are 36° to 57° C./23 mmHg, 82° to 84° C./12 mmHg, 82° to 86° C./10 mmHg, 86° to 90° C./8 mmHg and 90° to 97° C./7 mmHg, respectively.

TABLE 1

| Fraction No. | Weight (g) | DMF (%) | 1,5-dichloro-pentane (%) | 1-bromo-5-chloro-pentane (%) | 1,5-dibromo-pentane (%) |
|---|---|---|---|---|---|
| 1 | 87 | 94 | 5 | — | — |
| 2 | 75 | 2 | 86 | 8 | — |
| 3 | 50 | — | 59 | 41 | — |
| 4 | 130 | — | 1 | 96 | 1 |
| 5 | 120 | — | — | 20 | 76 |
| Residue | 8 | | | | |

EXAMPLE 2

Synthesis of 1-bromo-6-chlorohexane

In a reactor, 155 g (1 mole) of 1,6-dichlorohexane, 244 g (1 mole) of 1,6-dibromohexane and 150 g of DMAC were charged, followed by stirring at 110° C. for three hours. After the completion of the reaction, the reaction mixture was analyzed by gas chromatography. As a result, the reaction mixture was found to comprise 24.2% of DMAC, 18.0% of 1,6-dichlorohexane, 39.3% of 1-bromo-6-chlorohexane and 18.5% of 1,6-dibromohexane. The conversion degree was 51.8%.

The reaction mixture was then fractionated by a rectifying column, whereby 1-bromo-6-chlorohexane was isolated as shown in Table 2. In Table 2, the boiling points of Fraction 1, Fraction 2, Fraction 3, Fraction 4 and Fraction 5 are 45° to 59° C./20 mmHg, 59° to 84° C./10 mmHg, 84° to 90° C./6 mmHg, 90° to 92° C./6 mmHg and 93° to 97° C./5 mmHg, respectively.

TABLE 2

| Fraction No. | Weight (g) | DMAC (%) | 1,6-dichloro-hexane (%) | 1-bromo-6-chloro-hexane (%) | 1,6-dibromo-hexane (%) |
|---|---|---|---|---|---|
| 1 | 145 | 96 | 3 | — | — |
| 2 | 86 | 3 | 78 | 18 | — |
| 3 | 51 | — | 41 | 57 | — |
| 4 | 148 | — | 1 | 96 | 2 |
| 5 | 109 | — | — | 13 | 86 |
| Residue | 10 | | | | |

EXAMPLE 3

Synthesis of 1-bromo-8-chlorooctane

In a reactor, 36.6 g (0.2 mole) of 1,8-dichlorooctane, 54.4 g (0.2 mole) of 1,8-dibromooctane and 40 g of DMI were charged, followed by stirring at 140° C. for three hours in a nitrogen gas atmosphere. After the completion of the reaction, the reaction mixture was analyzed by gas chromatography. As a result, the reaction mixture was found to comprise 18.7% of DMI, 21.8% of 1,8-dichlorooctane, 40.0% of 1-bromo-8-chlorooctane and 17.9% of 1,8-dibromooctane. The conversion degree was 50.7%.

COMPARATIVE EXAMPLE 1

In a similar manner to Example 1 except that 100 g of DMF were not added, the reaction and analysis were effected. As a result, only a trace amount of 1-bromo-5-chloropentane was detected.

COMPARATIVE EXAMPLE 2

Synthesis of 1-bromo-6-chlorohexane

In a reactor, 240 g (2 mole) of 1,6-hexanediol, 156 g of 35% hydrochloric acid and 1 g of $ZnCl_2$ were charged, followed by stirring at 98° C. for 8 hours. After the reaction mixture was extracted with 200 ml of toluene, the toluene layer was washed with 200 ml of a 5% aqueous solution of sodium hydroxide, followed by fractionation, whereby 93.5 g (yield: 34%, purity: 98%) of 6-chloro-1-hexanol were obtained. In 200 ml of hexane, 93.5 g (0.68 mole) of the resulting 6-chloro-1-hexanol were poured, followed by the dropwise addition of 64 g (0.236 mole) of $PBr_3$ at 40° C. or lower to cause reaction. After the completion of the reaction, the reaction mixture was washed successively with 200 g of pure water and 300 g of a 3% aqueous solution of sodium hydroxide and n-hexane was removed. As a result of the analysis of the concentrate by gas chromatography, it was found to comprise 2% of 1,6-dichlorohexane, 4% of 1,6-dibromohexane and 93% of 1-bromo-6-chlorohexane. The concentrate was then fractionated in a rectifying column. The results are shown in Table 3.

In Table 3, the boiling points of Fraction 1, Fraction 2 and Fraction 3 are 80° to 90° C./6 mmHg, 89° to 95° C./6 mmHg and 95° to 98° C./6 mmHg, respectively.

TABLE 3

| Fraction No. | Weight (g) | 1,6-dichloro-hexane (%) | 1-bromo-6-chloro-hexane (%) | 1,6-dibromo-hexane (%) |
|---|---|---|---|---|
| 1 | 23 | 12 | 86 | 1 |
| 2 | 43 | 2 | 86 | 10 |
| 3 | 11 | 2 | 63 | 27 |
| Residue | 37 | | | |

We claim:
1. A process for the preparation of an α-bromo,ω-chloroalkane, represented by the formula $Br(CH_2)_nCl$, which comprises reacting in an organic solvent an α,ω-dichloroalkane, represented by the formula $Cl(CH_2)_nCl$, with an α,ω-dibromoalkane, represented by the formula $Br(CH_2)_nBr$, wherein n is an integer from 4 to 12.
2. A process according to claim 1, wherein the organic solvent is an aprotic organic solvent having a dielectric constant at 20° C. of 20 or higher.
3. A process according to claim 2, wherein the organic solvent is a nitrogen-containing organic solvent or a sulfur-containing organic solvent.
4. A process according to claim 1, wherein the organic solvent is selected from the group consisting of N,N-dimethylformamide, N,N-dimethylacetamide and N,N-dimethylimidazolidinone.

* * * * *